(12) United States Patent
Enomoto

(10) Patent No.: US 8,748,834 B2
(45) Date of Patent: Jun. 10, 2014

(54) RADIOGRAPHIC IMAGE CAPTURE SYSTEM AND METHOD

(75) Inventor: Jun Enomoto, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 214 days.

(21) Appl. No.: 13/137,213

(22) Filed: Jul. 28, 2011

(65) Prior Publication Data

US 2012/0049080 A1    Mar. 1, 2012

(30) Foreign Application Priority Data

Aug. 26, 2010 (JP) ................................. 2010-189697

(51) Int. Cl.
*G01T 1/24* (2006.01)

(52) U.S. Cl.
USPC ................................................... 250/370.08

(58) Field of Classification Search
USPC ........................................ 250/370.08, 370.09
See application file for complete search history.

(56) References Cited

U.S. PATENT DOCUMENTS

| | | | | |
|---|---|---|---|---|
| 7,737,427 | B2 * | 6/2010 | Kito et al. ....................... | 250/580 |
| 2003/0048938 | A1 | 3/2003 | Wang et al. | |
| 2006/0219926 | A1 * | 10/2006 | Shoji et al. ............... | 250/370.09 |
| 2007/0297567 | A1 * | 12/2007 | Takenaka et al. ............ | 378/98.2 |
| 2008/0239115 | A1 * | 10/2008 | Sugizaki ......................... | 348/246 |
| 2008/0279334 | A1 * | 11/2008 | Takenaka et al. ............. | 378/116 |
| 2009/0026392 | A1 * | 1/2009 | Yoshimi et al. ................ | 250/582 |
| 2009/0028298 | A1 * | 1/2009 | Ohta et al. ..................... | 378/165 |
| 2009/0034683 | A1 | 2/2009 | Tamakoshi | |
| 2009/0189761 | A1 * | 7/2009 | Nishino et al. ................. | 340/540 |
| 2009/0256915 | A1 * | 10/2009 | Harada et al. ................. | 348/162 |
| 2010/0034356 | A1 * | 2/2010 | Hayashida ...................... | 378/98 |
| 2010/0054416 | A1 * | 3/2010 | Tsubota et al. ................. | 378/98 |
| 2010/0080437 | A1 * | 4/2010 | Yoshida et al. ............... | 382/132 |
| 2010/0140490 | A1 * | 6/2010 | Tsubota et al. ........... | 250/370.08 |
| 2010/0208970 | A1 * | 8/2010 | Hattori et al. ................. | 382/132 |
| 2011/0026677 | A1 * | 2/2011 | Konishi ..................... | 378/98.12 |

FOREIGN PATENT DOCUMENTS

| | | |
|---|---|---|
| DE | 102007025448 A1 | 12/2008 |
| JP | 3-287249 | 12/1991 |
| JP | 2002-200064 | 7/2002 |

(Continued)

OTHER PUBLICATIONS

Notice of Reasons for Rejection issued by the Japanese Patent Office (JPO) on Nov. 19, 2013 in connection with Japanese Patent Application No. 2010-189697.

*Primary Examiner* — David Porta
*Assistant Examiner* — Taeho Jo
(74) *Attorney, Agent, or Firm* — Jean C. Edwards; Edwards Neils PLLC

(57) ABSTRACT

A radiographic image capture system includes: a radiographic image capture section, an output section and a generation section. The radiographic image capture section has plural radiographic imaging devices are placed adjacent to each other in a predetermined direction. Each of the radiographic imaging devices independently performs an imaging action, a preparatory action that is performed before the imaging action, and a transition action in which the radiographic imaging device transitions, in response to a transition command, from a first state in which the radiographic imaging device performs the preparatory action to a second state in which the radiographic imaging device performs the imaging action. The output section outputs the transition command to the plurality of radiographic imaging devices when imaging condition data has been input. The generation section combines image data acquired by the radiographic imaging devices and generates elongated image data representing an elongated radiographic image.

8 Claims, 8 Drawing Sheets

(56) References Cited

FOREIGN PATENT DOCUMENTS

| | | |
|---|---|---|
| JP | 2003-126071 A | 5/2003 |
| JP | 2004-180931 A | 7/2004 |
| JP | 2005-270277 | 10/2005 |
| JP | 2007-061385 A | 3/2007 |
| WO | WO 2004/032481 A2 | 4/2004 |

* cited by examiner

FIG.6

IMAGING MENU INPUT SCREEN 100

PLEASE INPUT THE NAME OF THE EXAMINEE, THE IMAGING SITE, THE IMAGING POSTURE, AND THE EXPOSURE CONDITIONS.

MR. OR MRS.
IMAGING SITE
IMAGING POSTURE

EXPOSURE CONDITIONS
- TUBE VOLTAGE
- TUBE CURRENT
- DURATION OF EXPOSURE

END

FIG.8
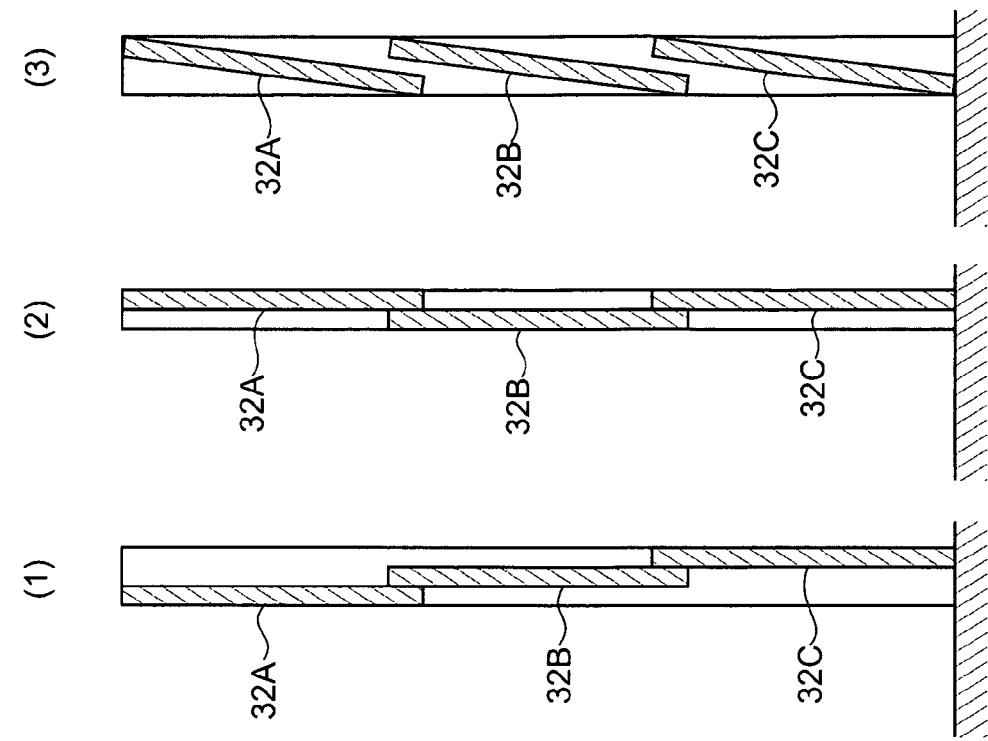
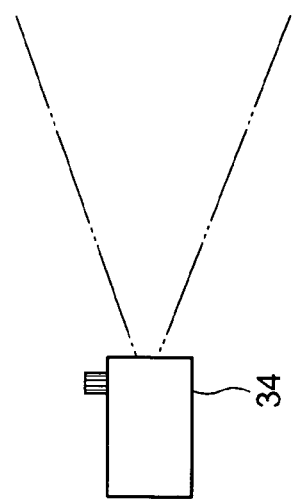

RADIOGRAPHIC IMAGE CAPTURE SYSTEM AND METHOD

CROSS-REFERENCE TO RELATED APPLICATION

This application claims priority under 35 USC 119 from Japanese Patent Application No. 2010-189697 filed on Aug. 26, 2010, the disclosure of which is incorporated by reference herein.

BACKGROUND OF THE INVENTION

1. Field of the Invention

The present invention relates to a radiographic image capture system and method that perform capture of radiographic images represented by radiation that has been emitted from a radiation source and has passed through a subject.

2. Description of the Related Art

In recent years, radiation detectors such as a flat panel detector (FPD), in which a radiation-sensitive layer is placed on a thin-film transistor (TFT) active matrix substrate and which can convert radiation directly into digital data, have been put into practical use. Portable radiographic imaging devices (hereinafter also called "electronic cassettes") that use these radiation detectors to detect applied radiation and capture radiographic images expressed by the radiation have also been put into practical use. Methods of converting the radiation in the radiation detectors used in the electronic cassettes include an indirect conversion method, in which a scintillator is used to convert the radiation into light and thereafter a semiconductor layer of a photodiode or the like is used to convert the light into electric charges, and a direct conversion method, in which a semiconductor layer of amorphous selenium or the like is used to convert the radiation into electric charges. There exist various types of materials that can be used for the semiconductor layer in each of these methods.

In this way, radiographic image capture systems are becoming increasingly digitized and are undergoing a transition from film and imaging plates to systems using radiation detectors.

Incidentally, in performing full-length lower-extremity imaging and whole-spine imaging for the purpose of bone measurements and so forth to capture images for medical use, the imaging site of the subject covers a wide range, so it is necessary to perform long-length (elongated) imaging in order to grasp the whole. In order to perform such long-length imaging, there is known a radiographic image information recording and reading device in which plural photostimulable phosphor sheets are arranged such that they partially overlap each other and which performs capture of elongated radiographic images (e.g., see Japanese Patent Application Laid-Open No. 3-287249).

Further, in image capture systems using a radiation detector, there is known a radiographic imaging apparatus equipped with a parallel moving mechanism, which enables at least either one of an electronic cassette or a subject to move substantially parallel with respect to the body axis direction of the subject, and a linked moving mechanism, which causes a radiation source to move to a position opposing a radiographic image detector so as to link the radiation source to the movement of the radiographic image detector, wherein the radiation source is configured to apply radiation with respect to the radiographic image detector in plural positions in which its position relative to the subject is different (e.g., see JP-A No. 2005-270277).

However, in the technology disclosed in JP-A No. 2005-270277, image capture is performed multiple times in different positions, so a mechanism for moving the electronic cassette becomes necessary, the apparatus becomes larger in scale, and the cost of the apparatus will be high. By interconnecting plural electronic cassettes, long-length imaging can be performed in the same way as with the technology of JP-A No. 3-287249. However, in the case of using a structure that electrically interconnects and synchronizes the radiation generator and each of the electronic cassettes and a structure that synchronizes each of the electronic cassettes with each other, it is necessary to perform capture of a radiographic image by each of the electronic cassettes in synchronization with the timing when the radiation is emitted from the radiation source. For this reason, it is necessary to electrically interconnect the radiation source and the electronic cassettes and also to electrically interconnect each of the plural electronic cassettes to each other, and the configuration for interconnecting the radiation source and the electronic cassettes, the configuration for interconnecting the plural electronic cassettes to each other, and timing control become complicated.

SUMMARY

The present invention has been made in consideration of the above and provides a radiographic image capture system and method which, when using plural radiographic imaging devices to capture a elongated radiographic image, can capture the elongated radiographic image without having to electrically interconnect and synchronize the radiation source and each of the radiographic imaging devices and without having to synchronize the plural radiographic imaging devices with each other.

One aspect of the present invention is a radiographic image capture system including: a radiographic image capture section in which plural radiographic imaging devices are placed adjacent to each other in a predetermined direction, with each of the radiographic imaging devices independently performing an imaging action in which the radiographic imaging device detects radiation that has been applied from a radiation source and has passed through a subject to acquire image data representing a radiographic image of the subject, a preparatory action that is performed before the imaging action, and a transition action in which the radiographic imaging device transitions, in response to a transition command, from a first state in which the radiographic imaging device performs the preparatory action to a second state in which the radiographic imaging device performs the imaging action; an output section that outputs the transition command to the plurality of radiographic imaging devices in a case in which imaging condition data has been input; and a generation section that combines image data acquired by each of the radiographic imaging devices transitioned to the second state by the transition command, to generate elongated image data representing an elongated radiographic image.

In this way, in this aspect, the transition command is output in a case in which the information representing the imaging conditions has been input, and each of the plural radiographic imaging devices transitions, independent of one another, from the first state to the second state due to the transition command. Then, the generation section combines the image data that have been acquired by each of the radiographic imaging devices that have been transitioned to the second state by the transition command to generate the elongated image data. Because of this, an elongated radiographic image can be captured without electrically synchronizing the radiation source and each of the radiographic imaging devices, and without synchronizing the plural radiographic imaging devices with each other.

In the above aspect, the preparatory action may include repeatedly performing, until the transition command is input, a reset action in which electric charges stored in the radiographic imaging devices are discharged. Because of this, a radiographic image with even higher image quality can be obtained.

In the above aspect, the radiographic image capture system may further include: an acquisition section that acquires correction image data as a result of imaging being performed by the radiographic imaging devices in a state in which the radiation from the radiation source is not made incident thereon; and a correction section that corrects the image data or the elongated image data using the correction image data. Because of this, a radiographic image with even higher image quality can be obtained.

In the above aspect, the radiographic imaging devices may be portable radiographic imaging devices.

In the above configuration, elongated image data can be obtained without electrically synchronizing the application of the radiation from the radiation source and each of the radiographic imaging devices. Therefore, even when each of the radiographic imaging devices is portable, long-length imaging can be feasibly performed because a complicated connection configuration and timing control are unnecessary. For example, long-length imaging can also be performed utilizing radiographic imaging devices in an unused imaging system.

Another aspect of the present invention is a radiographic image capture method including: providing plural radiographic imaging devices in a state in which the radiographic imaging devices are placed adjacent to each other in a predetermined direction, with each of the radiographic imaging devices independently performing an imaging action in which the radiographic imaging device detects radiation that has been applied from a radiation source and has passed through a subject to acquire image data representing a radiographic image of the subject, a preparatory action that is performed before the imaging action, and a transition action in which the radiographic imaging device transitions, in response to a transition command, from a first state in which the radiographic imaging device performs the preparatory action to a second state in which the radiographic imaging device performs the imaging action; outputting the transition command to the plurality of radiographic imaging devices in a case in which imaging condition data has been input; and combining image data acquired by each of the radiographic imaging devices transitioned to the second state by the transition command to generate elongated image data representing an elongated radiographic image.

With this aspect, an elongated radiographic image can also be captured without electrically synchronizing the radiation source and each of the radiographic imaging devices, and without synchronizing the plural radiographic imaging devices with each other.

In the above aspect, the preparatory action may include repeatedly performing, until the transition command is input, a reset action in which electric charges stored in the radiographic imaging devices are discharged.

Because of this, a radiographic image with even higher image quality can be obtained.

In the above aspect, the radiographic image capture method may further include: acquiring correction image data as a result of imaging being performed by the radiographic imaging devices in a state in which the radiation from the radiation source is not made incident thereon; and correcting the image data or the elongated image data using the correction image data.

Because of this, a radiographic image with even higher image quality can be obtained.

In the above aspect, the radiographic imaging devices may be portable radiographic imaging devices.

In the above configuration, elongated image data can be obtained without electrically synchronizing the application of the radiation from the radiation source and each of the radiographic imaging devices. Therefore, even when each of the radiographic imaging devices is portable, long-length imaging can be feasibly performed because a complicated connection configuration and timing control are unnecessary. For example, long-length imaging can also be performed utilizing radiographic imaging devices in an unused imaging system.

In this way, according to the above aspects, when using plural radiographic imaging devices to capture a elongated radiographic image, the elongated radiographic image can be captured without electrically interconnecting and synchronizing the radiation source and each of the radiographic imaging devices, and without synchronizing the plural radiographic imaging devices with each other.

BRIEF DESCRIPTION OF THE DRAWINGS

An exemplary embodiment of the present invention will be described in detail based on the following figures, wherein:

FIG. 6 is a schematic diagram showing an example of an imaging menu input screen that is displayed by the execution of the radiographic image capture program pertaining to the exemplary embodiment;

FIG. 8 is a diagram schematically showing another example placement of the electronic cassettes.

DETAILED DESCRIPTION

An exemplary embodiment of the present invention will be described in detail below with reference to the drawings. Here, an example of a case in which the present invention is applied to a radiology information system, which is a system that as a whole manages information handled in a radiology department in a hospital, will be described.

Figure 1:
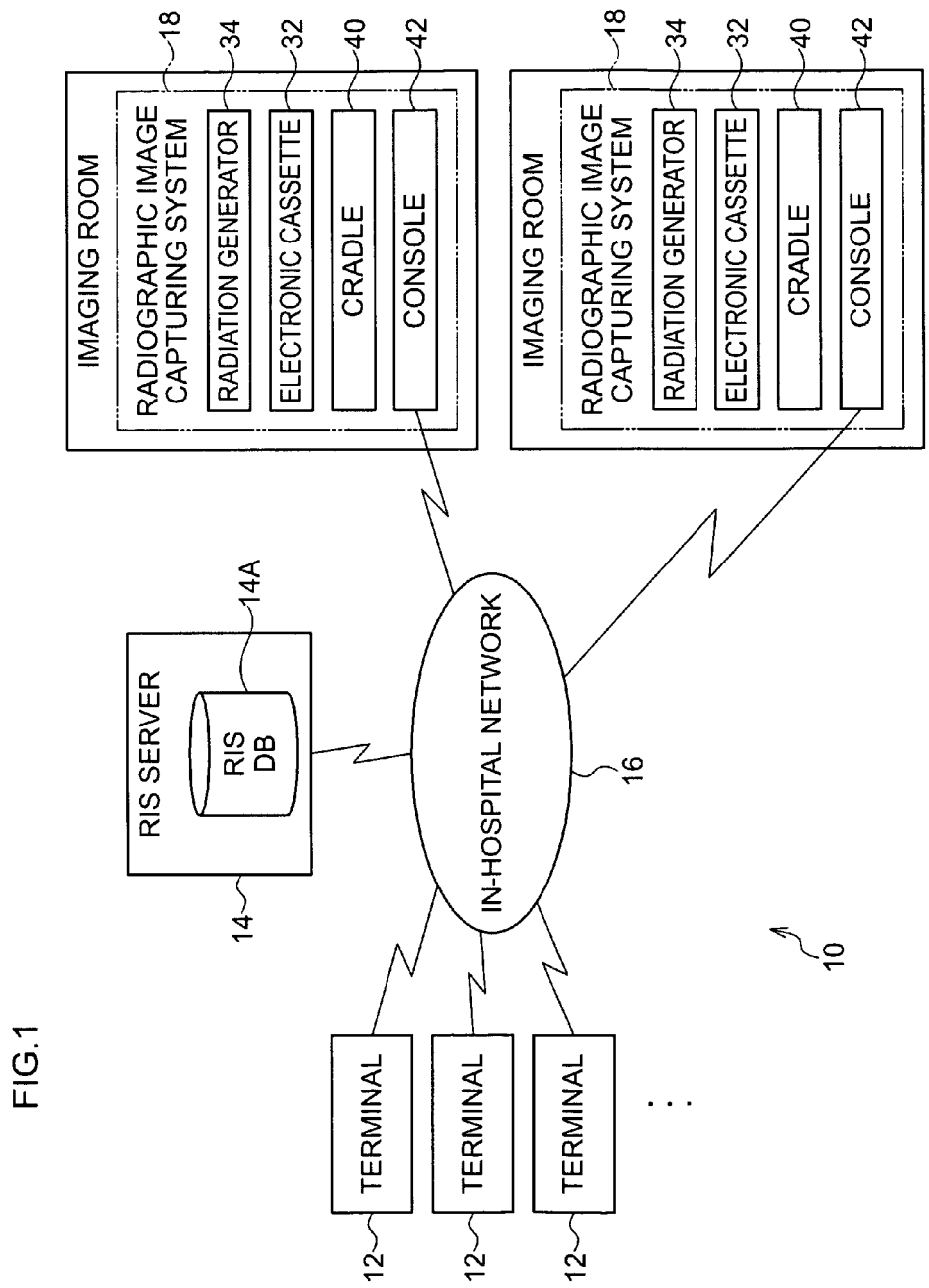
FIG. 1 is a block diagram showing the configuration of a radiology information system pertaining to the exemplary embodiment.

First, the configuration of a radiology information system (RIS) 10 (hereinafter called "the RIS 10") pertaining to the present exemplary embodiment will be described with reference to FIG. 1.

The RIS 10 is a system for managing information such as medical service appointments and diagnostic records in a radiology department and configures part of a hospital information system (hereinafter called "the HIS").

The RIS 10 has plural imaging request terminals 12 (hereinafter called "the terminal(s) 12"), an RIS server 14, and radiographic image capture systems 18 (hereinafter called "the imaging system(s) 18"). The imaging systems 18 are installed in individual radiographic imaging rooms (or operating rooms) in a hospital. The RIS 10 is configured as a result of the terminals 12, the RIS server 14, and the imaging systems 18 being connected to an in-hospital network 16 comprising a wired or wireless local area network (LAN). The RIS 10 configures a part of the HIS disposed in the same hospital, and an HIS server (not shown) that manages the entire HIS is also connected to the in-hospital network 16.

The terminals 12 are for doctors or radiologic technologists to input and browse diagnostic information and facility reservations. Radiographic imaging requests and imaging reservations are also made via these terminals 12. Each of the terminals 12 is configured to include a personal computer having a display device, and the terminals 12 are connected by the in-hospital network 16 to the RIS server 14 so as to be capable of communicating with each other.

The RIS server 14 receives the imaging requests from each of the terminals 12 and manages radiographic imaging schedules in the imaging systems 18. The RIS server 14 is configured to include a database 14A.

The database 14A stores patient-related information (data), such as attribute information (names, sexes, dates of birth, ages, blood types, body weights, patient identifications (IDs), etc.) of examinees (patients) serving as subjects, their medical histories, their consultation histories, and radiographic images of those patients that have been captured in the past.

The database 14A is also configured to include information relating to later-described electronic cassettes 32—such as their identification numbers (ID information), models, sizes, sensitivities, usable imaging sites (the content of imaging requests they can accommodate), dates of first use, and numbers of times used—used in the imaging systems 18 and environment information representing the environments in which the electronic cassettes 32 are used to capture radiographic images, that is, the environments in which the electronic cassettes 32 are used (for example, radiographic imaging rooms or operating rooms).

The imaging systems 18 perform capture of radiographic images as a result of being operated by the doctors or the radiologic technologists in response to an instruction from the RIS server 14. Each of the imaging systems 18 is equipped with a radiation generator 34, a portable radiographic imaging device (hereinafter "electronic cassette") 32, a cradle 40, and a console 42. The radiation generator 34 (see also FIG. 2) irradiates a subject with a dose of radiation X according to exposure conditions from a radiation source 130 (see also FIG. 4). The electronic cassette 32 has a built-in radiation detector 60 (see also FIG. 3) that detects the radiation X that has passed through an imaging target site of the subject, generates electric charges, and generates image information (data) representing a radiographic image on the basis of the generated electric charge quantity. The cradle 40 charges a battery that is built into the electronic cassette 32. The console 42 controls the electronic cassette 32, the radiation generator 34, and the cradle 40.

The console 42 can acquire various types of information (data) included in the database 14A from the RIS server 14, store the data in a later-described HDD 110 (see FIG. 4), and control the electronic cassette 32, the radiation generator 34, and the cradle 40 on the basis of this data.

Figure 2:
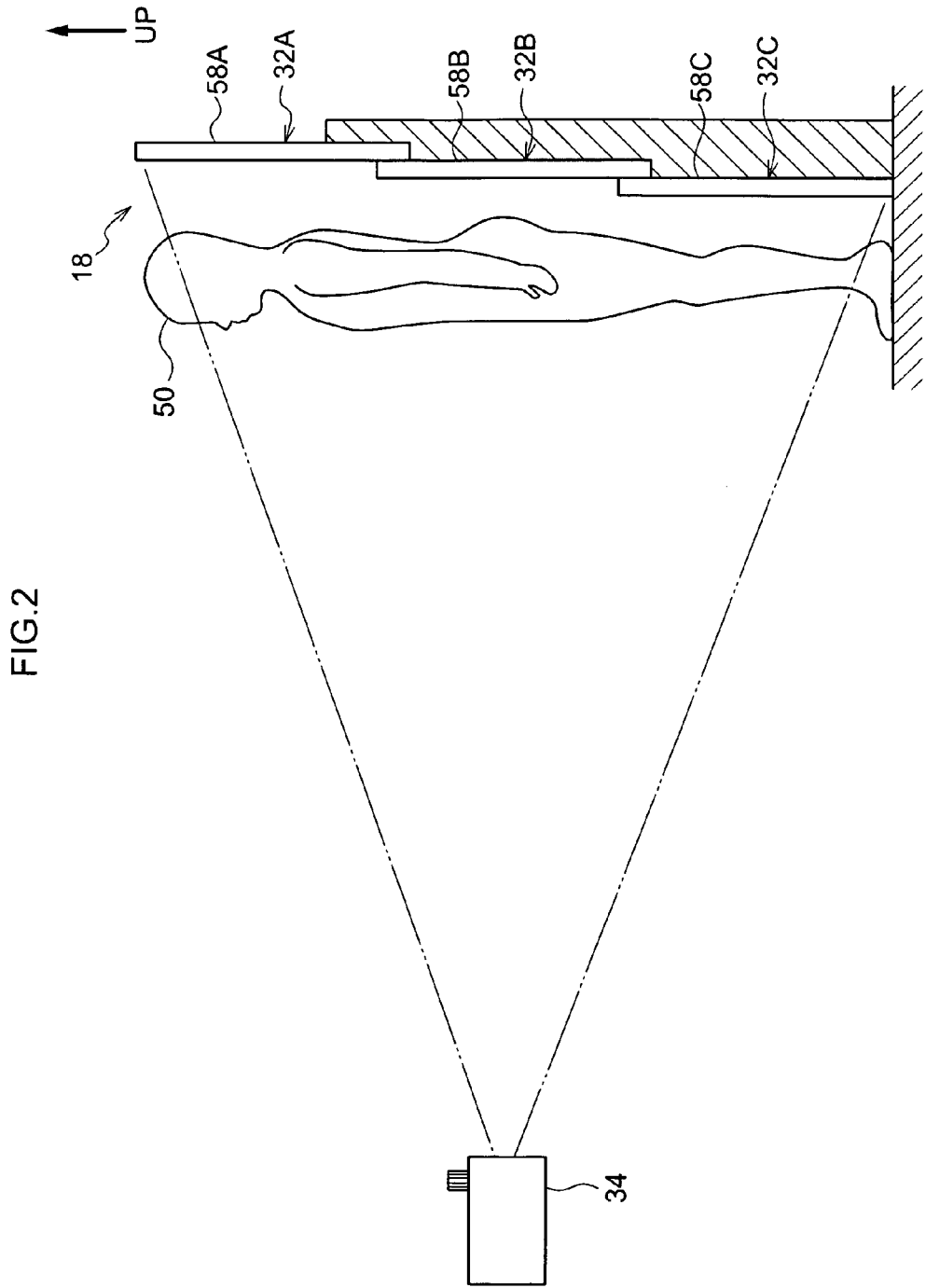
FIG. 2 is a side view showing an example placement of devices in a radiographic imaging room of a radiographic image capture system pertaining to the exemplary embodiment.

In FIG. 2, there is shown an example placement of the radiation generator 34 and plural electronic cassettes 32 (here, three of the electronic cassettes 32 including a first electronic cassette 32A, a second electronic cassette 32B, and a third electronic cassette 32C are shown) in the imaging system 18 pertaining to the present exemplary embodiment. Arrow UP in the drawing represents up in a vertical direction.

In the present exemplary embodiment, the basic configurations of the first electronic cassette 32A, the second electronic cassette 32B, and the third electronic cassette 32C are the same, so in cases in which it is not particularly necessary to distinguish between these electronic cassettes 32, the electronic cassettes 32 will be identified as simply "the electronic cassette(s) 32" without being preceded by "first", "second", and "third" and without the numeral "32" being followed by "A", "B", and "C". The same will hold true for the components configuring the electronic cassettes 32.

Next, the configuration of the electronic cassettes 32 will be described with reference to FIG. 3 and FIG. 4.

Figure 3:
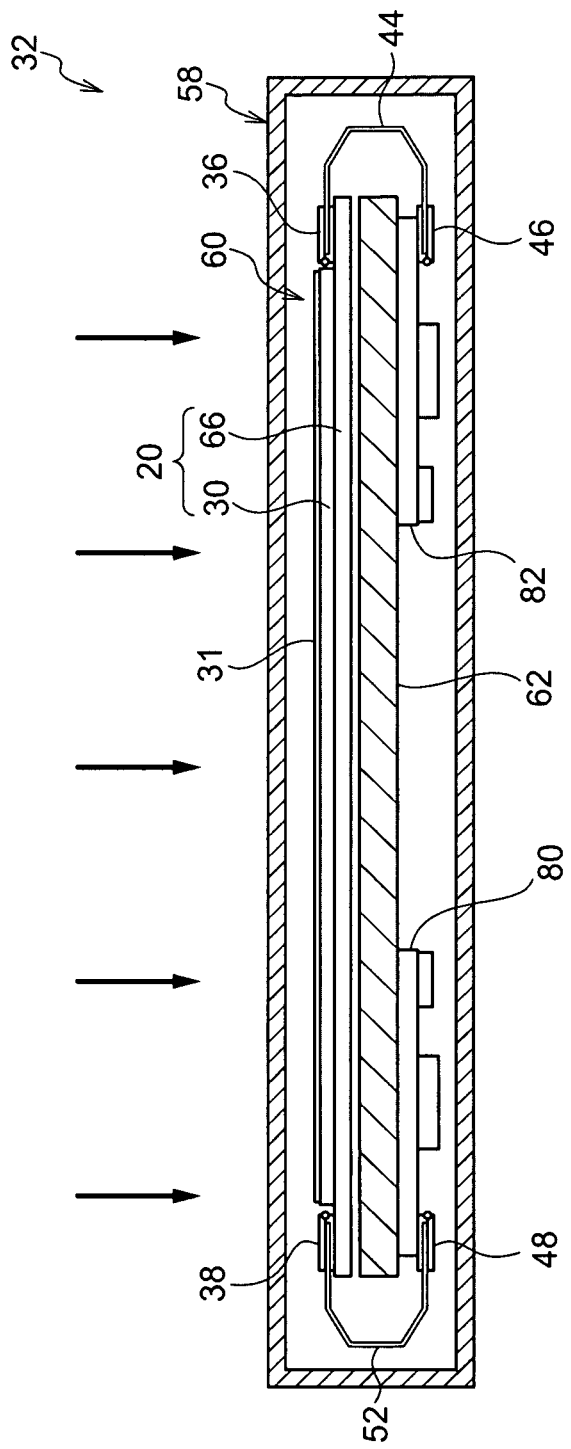
FIG. 3 is a cross-sectional view showing the internal configuration of an electronic cassette pertaining to the exemplary embodiment.

As shown in FIG. 3, each of the electronic cassettes 58 is equipped with a casing 58. A radiation imaging layer 20 is disposed inside the casing 58. The radiation imaging layer 20 is equipped with a TFT active matrix substrate 66 and a scintillator 30. The TFT active matrix substrate 66 is equipped with an upper electrode, a semiconductor layer, and a lower electrode. Further, a photoelectric conversion element (photodiode) layer (hereinafter "photoelectric conversion layer") (not shown in FIG. 3) is disposed between the TFT active matrix substrate 66 and the scintillator 30. The scintillator 30 is formed of GOS or CsI or the like. Applied radiation is converted into light by the scintillator 30, the light is then converted into electric charges by the photoelectric conversion layer, and those electric charges are stored in the TFT active matrix substrate 66. In order to prevent the light generated by the scintillator 30 from leaking to the outside, a light shield 31 that blocks the generated light is disposed on the face of the scintillator 30 on the opposite side of the face on which the TFT active matrix substrate 66 is disposed.

Further, as shown in FIG. 3, a control board 62 formed in a flat plate shape is disposed in the electronic cassette 32. A gate line driver 80 and a signal processor 82 are disposed on the control board 62. Plural connectors 46 are disposed on the signal processor 82, and one end of a flexible cable 44 is electrically connected to the connectors 46. A connector 36 disposed on the TFT active matrix substrate 66 is connected to the other end of the flexible cable 44. A connector 48 is disposed on the gate line driver 80, and one end of a flexible cable 52 is electrically connected to the connector 48. Moreover, the other end of the flexible cable 52 is connected to a connector 38 disposed on the TFT active matrix substrate 66.

Figure 4:
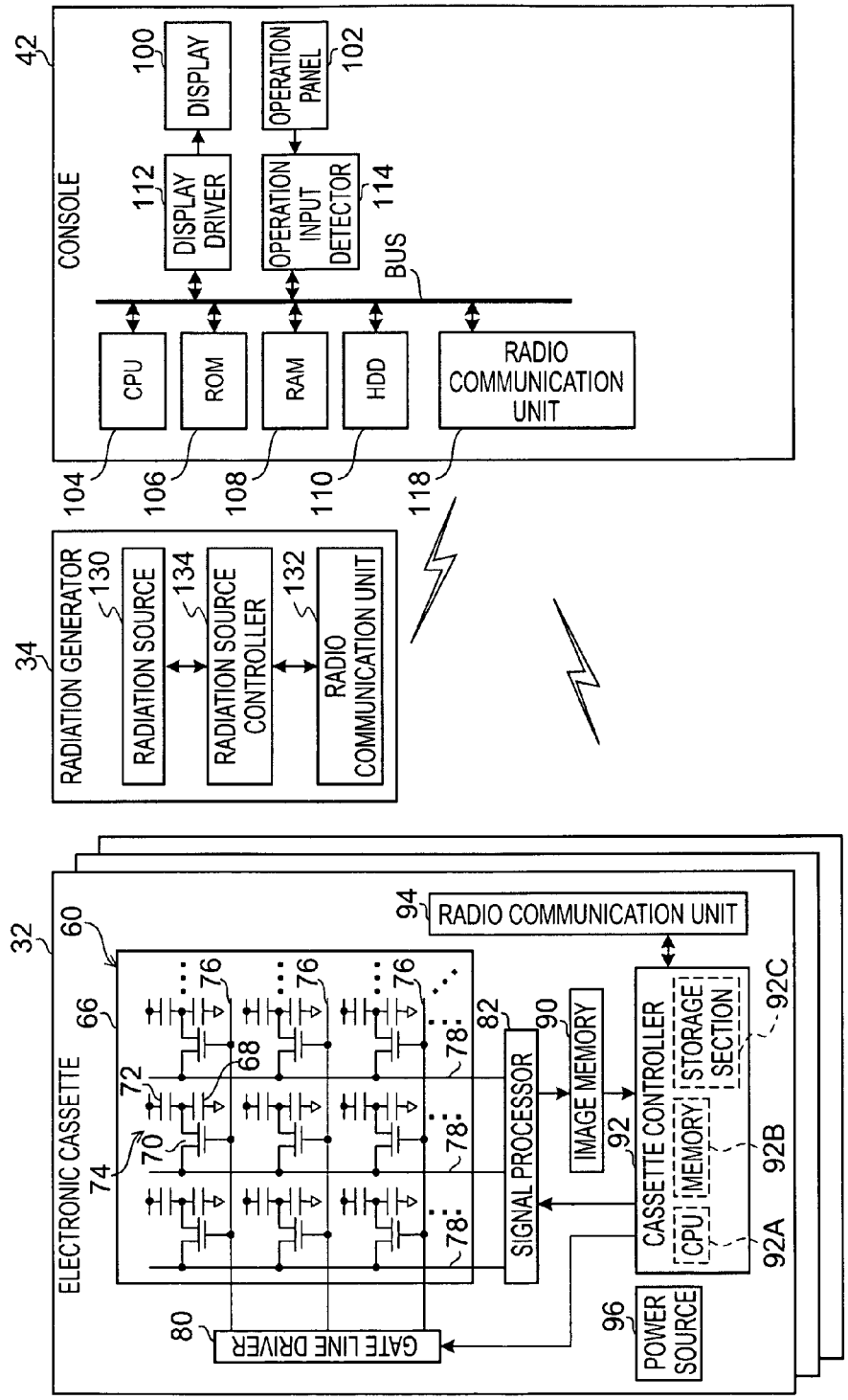
FIG. 4 is block diagram showing the configurations of main portions of an electrical system of the radiographic image capture system pertaining to the exemplary embodiment.

As shown in FIG. 4, numerous pixels 74 equipped with storage capacitors 68 and TFTs 70 are arranged in a matrix on the TFT active matrix substrate 66 (in FIG. 4, the photoelectric conversion layer corresponding to the individual pixels 74 is schematically shown as photoelectric converters 72). The storage capacitors 68 store the electric charges that have been generated in the photoelectric conversion layer. The TFTs 70 are for reading out the electric charges that have been stored in the storage capacitors 68. The electric charges that have been generated in the photoelectric conversion layer due to the application of the radiation X to the electronic cassette 32 are stored in the storage capacitors 68 of the respective pixels 74. Because of this, the image information that had been carried in the radiation X applied to the electronic cassette 32 is converted into electric charge information and is held in the radiation detector 60.

Here, the radiation detector 60, which uses a phosphor material (a scintillator) and a photoelectric conversion element (a photodiode) to indirectly convert the radiation X into electric charges, is taken as an example and described, but the radiation detector 60 is not limited to this. For example, the radiation detector 60 may also be one in which a photoelectric conversion layer that absorbs the radiation X and converts the radiation X into electric charges is layered on the TFT active matrix substrate 66, and, when the radiation X is applied, the radiation detector internally generates electric charges (electron-hole pairs) of an electric charge quantity corresponding to the applied dose of radiation to thereby convert the applied radiation X into electric charges. In this case, the photoelectric conversion layer can, for example, be configured from amorphous selenium (a-Se) that takes selenium as its main component (e.g., having a content percentage equal to or greater than 50%).

Plural gates lines 76 and plural data lines 78 are disposed on the TFT active matrix substrate 66. The plural gate lines 76 extend in one direction (row direction) and are for switching on and off the TFTs 70 of the respective pixels 74. The plural data lines 78 extend in a direction (column direction) orthogonal to the gate lines 76 and are for reading out the stored electric charges from the storage capacitors 68 via the TFTs 70 that have been switched on. The respective gate lines 76 are connected to the gate line driver 80 via the flexible cable 52, and the respective data lines 78 are connected to the signal processor 82. When the electric charges are stored in the storage capacitors 68 of the individual pixels 74, the TFTs 70 of the respective pixels 74 are sequentially switched on by row by signals that are supplied via the gate lines 76 from the gate line driver 80. The electric charges stored in the storage capacitors 68 of the pixels 74 whose TFTs 70 have been switched on are transmitted through the data lines 78 as analog electric signals and are input to the signal processor 82 via the flexible cable 44. Consequently, the electric charges stored in the storage capacitors 68 of the individual pixels 74 are sequentially read out by row.

The signal processor 82 is equipped with an amplifier and a sample-and-hold circuit for each of the data lines 78. The electric charge signals that have been transmitted through the respective data lines 78 are amplified by the amplifiers and are thereafter held in the sample-and-hold circuits. Further, a multiplexer and an analog-to-digital (A/D) converter are connected in this order to output sides of the sample-and-hold circuits. The electric charge signals held in the individual sample-and-hold circuits are sequentially (serially) input to the multiplexer and are converted into digital image data by the A/D converter.

An image memory 90 is connected to the signal processor 82. The image data that have been output from the A/D converter of the signal processor 82 are sequentially stored in the image memory 90. The image memory 90 has a storage capacity that is capable of storing plural frames' worth of image data. Each time capture of a radiographic imaging is performed, the image data obtained by the imaging are sequentially stored in the image memory 90.

The image memory 90 is connected to a cassette controller 92 that controls the operations of the entire electronic cassette 32. The cassette controller 92 is configured by a microcomputer and is equipped with a central processing unit (CPU) 92A, a memory 92B including a read-only memory (ROM) and a random access memory (RAM), and a nonvolatile storage section 92C that may be configured by a hard disk drive (HDD), a flash memory, or the like.

A radio communication unit 94 is connected to the cassette controller 92. The radio communication unit 94 pertaining to the present exemplary embodiment is adapted to a wireless local area network (LAN) standard represented by IEEE (Institute of Electrical and Electronics Engineers) 802.11a/b/g, for example, and controls the transmission of various types of information between the electronic cassette 32 and an external device by radio communication. The cassette controller 92 is made capable of radio communication with the console 42 via the radio communication unit 94 and is made capable of transmitting and receiving various types of information (data) to and from the console 42 via the radio communication unit 94.

A power source 96 is also disposed in the electronic cassette 32. The various circuits and elements mentioned above (such as the gate line driver 80, the signal processor 82, the image memory 90, the radio communication unit 94, and the cassette controller 92) are actuated by electrical power supplied from the power source 96. The power source 96 has a built-in battery (a rechargeable secondary battery) 96A so as to not impair the portability of the electronic cassette 32, and the power source 96 supplies electrical power to the various circuits and elements from the charged battery 96A. In FIG. 4, illustration of wires connecting the various circuits and elements to the power source 96 is omitted.

In the present exemplary embodiment, in the case of using three of the electronic cassettes 32 to perform long-length imaging as shown in FIG. 2, the upper end of a second casing 58B of the second electronic cassette 32B is superimposed on the front surface (the side on which the radiation is incident) of the lower end of a first casing 58A of the first electronic cassette 32A. Moreover, the upper end of a third casing 58C of the third electronic cassette 32C is superimposed on the front surface of the lower end of the second casing 58B of the second electronic cassette 32B. In this way, in the present exemplary embodiment, long-length imaging is performed by placing three of the electronic cassettes 32 adjacent to each other along the body axis direction of a subject 50 in a state in which the end portions of each of the adjacent electronic cassettes 32 have been superimposed on each other.

Each of the plural electronic cassettes 32 used in long-length imaging in this way independently performs an imaging action in which the electronic cassette 32 detects the radiation X that has been applied to the electronic cassette 32 from the radiation source 130 and has passed through a subject to acquire image data representing a radiographic image of the subject, a preparatory action (in the present exemplary embodiment, a reset action in which the electric charges stored in the radiation detector 60 are discharged) that is performed before the imaging action, and a transition action in which the electronic cassette 32 transitions from a first state in which the electronic cassette 32 performs the preparatory action to a second state in which the electronic cassette 32 performs the imaging action. The transition action is performed as a result of receiving a transition command (in the present exemplary embodiment, later-described instruction information (data) instructing each of the electronic cassettes 32 to start executing the imaging action).

The console 42 is configured as a server computer and is equipped with a display 100, which displays operation menus and radiographic images that have been captured, and an operation panel 102, which is configured to include plural keys and by which various types of information and operation instructions are input.

Further, the console 42 pertaining to the present exemplary embodiment is also equipped with a central processing unit (CPU) 104 that controls the operations of the entire device, a read-only memory (ROM) 106 in which various programs including a control program are stored beforehand, a random access memory (RAM) 108 that temporarily stores various types of data, a hard disk drive (HDD) 110 that stores and holds various types of data, a display driver 112 that controls the display of various types of information on the display 100, and an operation input detector 114 that detects states of operation with respect to the operation panel 102. Further, the console 42 is also equipped with a radio communication unit 118 that transmits and receives various types of data, such as later-described exposure conditions, to and from the radiation generator 34 by radio communication and also transmits and receives various types of data, such as image data, to and from the electronic cassettes 32 by radio communication.

The CPU 104, the ROM 106, the RAM 108, the HDD 110, the display driver 112, the operation input detector 114, and the radio communication unit 118 are interconnected via a system bus BUS. Consequently, the CPU 104 can access the ROM 106, the RAM 108, and the HDD 110, can control the display of various types of information on the display 100 via the display driver 112, and can control the transmission and reception of various types of data to and from the radiation generator 34 and the electronic cassettes 32 via the radio communication unit 118. Further, the CPU 104 can grasp states of operation by a user with respect to the operation panel 102 via the operation input detector 114.

The radiation generator 34 is equipped with the radiation source 130, a radio communication unit 132 that transmits and receives various types of data, such as the exposure conditions, to and from the console 42, and a radiation source controller 134 that controls the radiation source 130 on the basis of the received exposure conditions.

The radiation source control unit 134 is also realized by a microcomputer and stores the received exposure conditions and the like. The exposure conditions received from the console 42 include information such as tube voltage, tube current, duration of exposure, and so forth. The radiation source controller 134 causes the radiation source 130 to apply the radiation X on the basis of the received exposure conditions.

Next, processing that is executed in order to use the plural electronic cassettes 32 to perform long-length imaging will be described.

First, as shown in FIG. 2, the electronic cassettes 32 are placed adjacent to each other such that the end portions of the electronic cassettes 32 are superimposed and the imaging range extends in the vertical direction (the body axis direction of the subject 50). At this time, the subject 50 is standing along the electronic cassettes 32 that have been placed adjacent to each other in the vertical direction.

Figure 5:
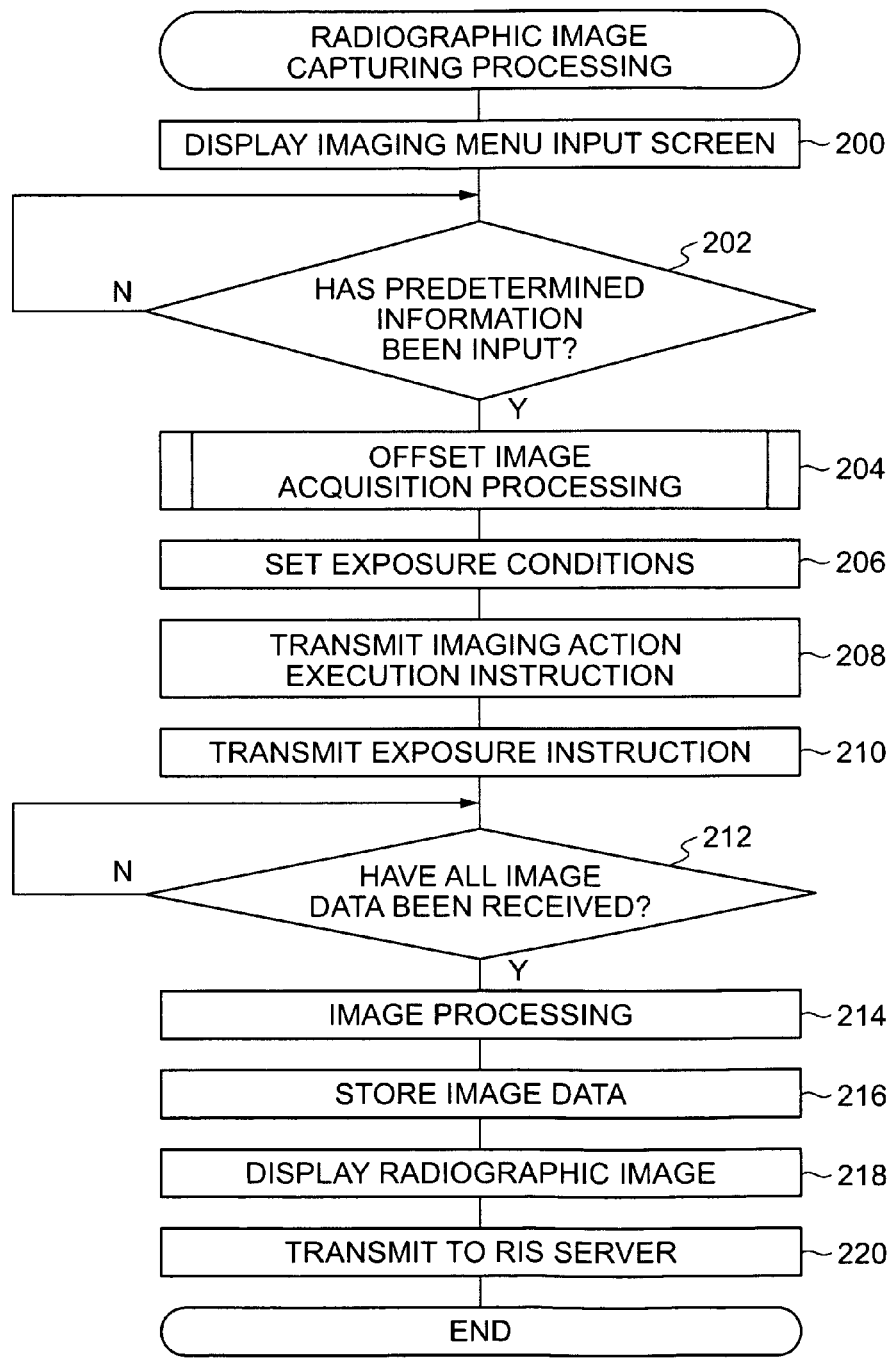
FIG. 5 is a flowchart showing a flow of a radiographic image capture program pertaining to the exemplary embodiment.

The CPU 104 of the console 42 executes the processing shown in FIG. 5. FIG. 5 is a flowchart showing a flow of processing by a radiographic image capture program that is executed by the CPU 104 of the console 42. This program is stored beforehand in a predetermined region of the ROM 106.

In step 200 of FIG. 5, the CPU 104 controls the display driver 112 so as to cause the display 100 to display a predetermined imaging menu input screen. In the next step 202, the processing waits for the input of predetermined information.

In FIG. 6, there is shown an example of the imaging menu input screen displayed by the display 100 by the processing in step 200. As shown in FIG. 6, a message prompting the input of an imaging menu serving as imaging conditions for capture of a radiographic image that is to be performed now and input fields for inputting these pieces of information are displayed in the imaging menu input screen pertaining to the present exemplary embodiment. The imaging menu includes, for example, the name of the examinee on which capture of a radiographic imaging is to be performed, the imaging site, the posture during imaging (in the present exemplary embodiment, a lying position or a standing position), and the exposure conditions of the radiation X during imaging (in the present exemplary embodiment, the tube voltage, the tube current, and the duration of exposure when applying the radiation X).

When the imaging menu input screen shown in FIG. 6 is displayed on the display 100, the radiographer inputs the imaging conditions (imaging menu) into the corresponding input fields via the operation panel 102 and thereafter designates, via the operation panel 102, the end button displayed near the lower end of the imaging menu input screen. When the end button is designated by the user, the determination in step 202 is YES and the processing moves to step 204.

In the next step 204, the CPU 104 executes, with respect to each of the electronic cassettes 32, offset image acquisition processing that acquires image data (hereinafter, "offset image data") for correcting image data (hereinafter, "subject image data") that have been obtained by the capture of a radiographic image by the radiation detector 60, by performing imaging by the radiation detector 60 in an electric charge storage period that is the same as an electric charge storage period (hereinafter, applied electric charge storage period) in the radiation detector 60 that is predetermined in accordance with the imaging site that has been inputted in the imaging menu input screen.

At this time, the CPU 104 transmits, together with data representing the applied electric charge storage period, instruction data instructing each of the electronic cassettes 32 to execute the offset image acquisition processing to each of the electronic cassettes 32 via the radio communication unit 118. In response to this, each of the electronic cassettes 32 performs the reset action in which the electric charges stored in the radiation detector 60 at this point in time are discharged, performs imaging by the radiation detector 60 in the received applied electric charge storage period, and transmits the offset image data obtained thereby to the console 42 via the radio communication unit 94.

The CPU 104 receives, via the radio communication unit 118, the offset image data that have been transmitted from each of the electronic cassettes 32 and stores the offset image data in a predetermined region of the RAM 108.

In the next step 206, the CPU 104 transmits the exposure conditions that have been input in the imaging menu input screen to the radiation generator 34 via the radio communication unit 118 to thereby set those exposure conditions. In response to this, the radiation source controller 134 makes preparations for exposure in the received exposure conditions.

In the next step 208, the CPU 104 transmits, to each of the electronic cassettes 32 via the radio communication unit 118, instruction data instructing each of the electronic cassettes 32 to start executing the imaging action. When each of the electronic cassettes 32 receives the instruction data, each of the electronic cassettes 32 transitions from the first state to the second state and starts executing the imaging action.

In the next step 210, the CPU 104 transmits, to the radiation generator 34 via the radio communication unit 118, instruction data instructing the radiation generator 34 to start exposure. In response to this, the radiation generator 34 generates and emits the radiation X from the radiation source 130 at the tube voltage, the tube current, and the duration of exposure corresponding to the exposure conditions that the radiation generator 34 received from the console 42 in step 206. Each of the electronic cassettes 32 performs capture of a radiographic image by the imaging action and transmits the subject image data that have been obtained thereby to the console 42 via the radio communication unit 94.

Therefore, in the next step 212, the CPU 104 stands by until the subject image data have been received from each of the electronic cassettes 32. In the next step 214, the CPU 104 executes, with respect to each of the sets of the subject image data that the CPU 104 has received, image processing that performs various types of correction such as shading correction after performing offset correction by subtracting per pixel the offset image data that the CPU 104 acquired by the processing in step 204. Further, the CPU 104 connects and combines each of the sets of the subject image data on which the image processing has been performed in this way to generate image data (hereinafter called composite image data) representing a elongated subject image.

In the next step 216, the CPU 104 stores in the HDD 110 the composite image data generated in step 214. In the next step 218, the CPU 104 controls the display driver 112 so as to cause the display 100 to display the radiographic image represented by the composite image data for checking and so forth. In the next step 220, the CPU 104 transmits the composite image data to the RIS server 14 via the in-hospital network 16. Thereafter, the CPU 104 ends the radiographic image capture program. The composite image data that have been transmitted to the RIS server 14 are stored in the database 14A so that it is possible for doctors to read and diagnosis the radiographic image that has been captured.

Figure 7:
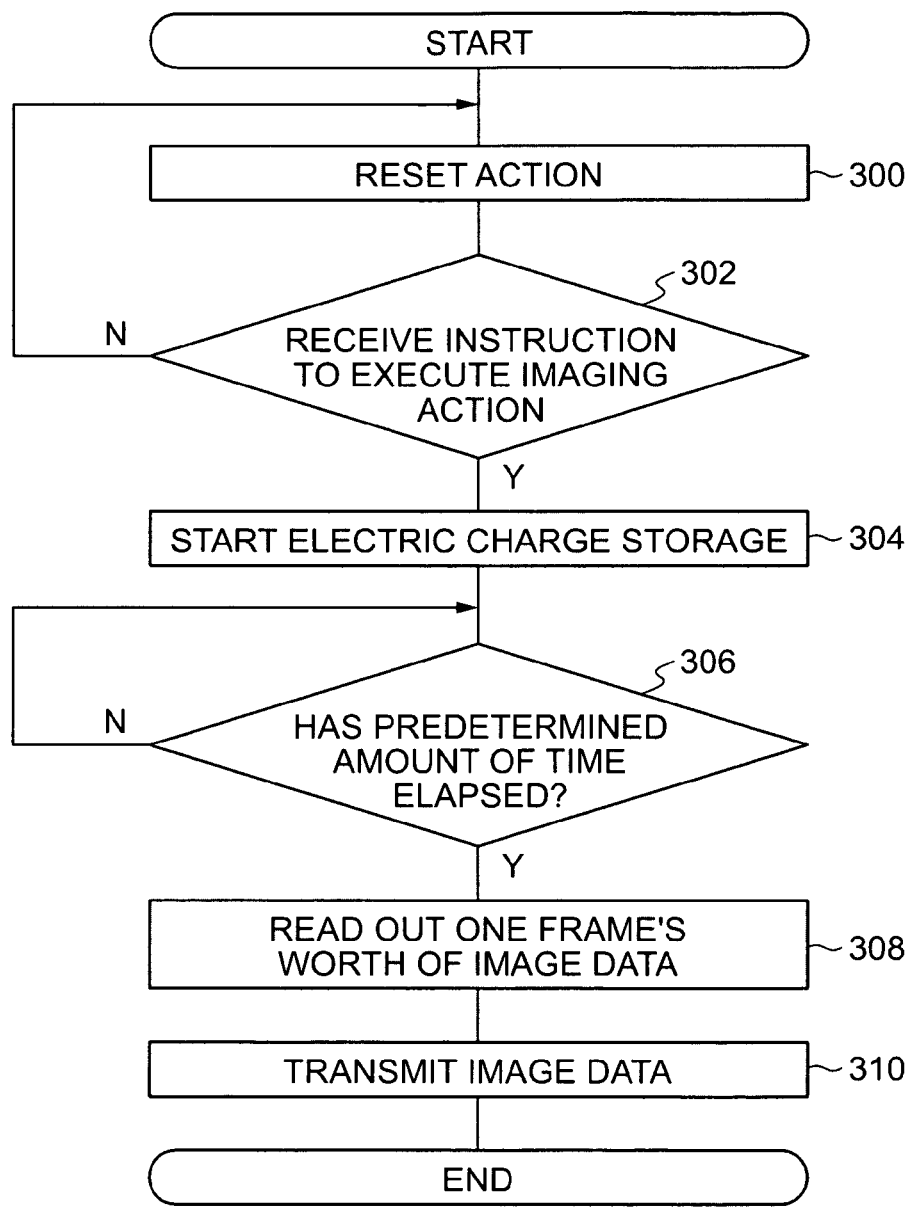
FIG. 7 is a flowchart showing a flow of processing that is performed in the electronic cassette pertaining to the exemplary embodiment.

Next, the action of each of the electronic cassettes 32 after the offset image acquisition processing will be described with reference to FIG. 7. FIG. 7 is a flowchart showing a flow of processing by a program that is executed by the CPU 92A disposed in the cassette controller 92 of each of the electronic cassettes 32. This program is stored beforehand in the storage section 92C of the cassette controller 92.

In step 300 of FIG. 7, the CPU 92A performs control so as to perform the reset action with respect to the radiation detector 60. In the next step 302, the CPU 92A judges whether or not it has received the instruction data instructing the CPU 92A to start executing the imaging action. In a case in which the CPU 92A has judged that it has not received the instruction data, the CPU 92A returns to step 300 and repeats the reset action. Further, in a case in which the CPU 92A has judged in step 302 that it has received the instruction data, the CPU 92A advances to step 304 where it performs control so as to start electric charge storage with respect to the radiation detector 60. In this way, each of the electronic cassettes 32 continues the first state in which it performs the reset action until it receives the instruction data, and when each of the electronic cassettes 32 receives the instruction data, it ends the reset action, starts electric charge storage, and transitions to the second state.

In the next step 306, the CPU 92A waits for the elapse of the applied electric charge storage period represented by information that the CPU 92A received together with the instruction data instructing the CPU 92A to execute the offset image acquisition processing.

In the next step 308, the CPU 92A performs control so as to read out the electric charges that have been stored at this point in time with respect to the radiation detector 60. In response to this, the electric charges flow out to each of the data lines 78 as electric signals from the radiation detector 60. The electric signals flowing out to each of the data lines 78 are converted into digital image data (the subject image data) by the signal processor 82, and the digital image data are stored in the image memory 90.

In the next step 310, the CPU 92A reads out the subject image data from the image memory 90 and transmits the subject image data to the console 42 via the radio communication unit 94. Thereafter, the CPU 92A ends the program.

As described in detail above, according to the present exemplary embodiment, in a case in which the imaging menu has been input, the console 42 transmits to each of the electronic cassettes 32 the transition command (in the present exemplary embodiment, the instruction data instructing each of the electronic cassettes 32 to start executing the imaging action) for causing each of the electronic cassettes 32 to transition from the first state to the second state, and in response to this instruction data, each of the electronic cassettes 32 transitions from the first state to the second state. Because of this, each of the electronic cassettes 32 transitions to the second state and starts the imaging action, so a elongated radiographic image can be obtained without electrically synchronizing the radiation generator 34 and the radiographic imaging devices (in the present exemplary embodiment, the electronic cassettes 32) and without synchronizing the electronic cassettes 32 with each other.

Further, according to the present exemplary embodiment, the console 42 acquires the correction image data (the offset image data) for correcting the image data (the subject image data) that have been obtained by the capture of a radiographic image by each of the electronic cassettes 32 in a state in which the radiation is not made incident, and uses the correction image data to correct the image data, so that a radiographic image with even higher image quality can be obtained.

The present invention has been described above using an exemplary embodiment, but the technical scope of the present invention is not limited to the scope described in the above exemplary embodiment. Various changes or improvements can be made to the above exemplary embodiment in a scope not departing from the gist of the invention, and the technical scope of the present invention also includes embodiments to which such changes or improvements have been made.

For example, as shown in (1) of FIG. 8, the electronic cassettes 32 may be placed such that the upper end of the second casing 18B of the second electronic cassette 32B is superimposed on the back surface (the opposite side with respect to the side on which the radiation is made incident) of the lower end of the first casing 18A of the first electronic cassette 32A and such that the upper end of the third casing 18C of the third electronic cassette 32C is superimposed on the back surface of the lower end of the second casing 18B of the second electronic cassette 32B.

Further, for example, as shown in (2) of FIG. 8, the electronic cassettes 32 may be placed such that the upper end of the second casing 18B of the second electronic cassette 32B is superimposed on the front surface (the side on which the radiation is made incident) of the lower end of the first casing 18A of the first electronic cassette 32A and such that the upper end of the third casing 18C of the third electronic cassette 32C is superimposed on the back surface of the lower end of the second casing 18B of the second electronic cassette 32B.

Further, for example, as shown in (3) of FIG. 8, the electronic cassettes 32 may be placed such that each of the electronic cassettes 32 is tilted a predetermined angle with respect to the vertical direction and such that the end portions of the electronic cassettes 32 that are adjacent to each other overlap when seen from the direction in which the radiation X is made incident.

The above exemplary embodiment has been described using three of the electronic cassettes 32, but the number of the electronic cassettes 32 is not particularly limited to three and may also be two or four or more.

Further, the above exemplary embodiment has been described using X-rays as the radiation, but the radiation is not particularly limited to this and may also be gamma rays or the like.

Further, in the above exemplary embodiment, the imaging systems 18 have been used for long-length imaging in a standing state, but the imaging systems may also be used for long-length imaging in a lying state. In this case, long-length imaging is possible by placing each of the electronic cassettes 32 so as to extend in the horizontal direction. Further, in the above exemplary embodiment, the electronic cassettes 32 have been made portable, but the electronic cassettes 32 may also be securely placed in the imaging systems 18 rather than being portable.

The above exemplary embodiment is not intended to limit the inventions pertaining to the claims, and not all combinations of features described in the exemplary embodiment are necessarily essential to the invention. The exemplary embodiment includes inventions of various stages, and various inventions can be extracted by appropriate combinations of the multiple configuration requirements disclosed. Even when several configuration requirements are omitted from all the configuration requirements disclosed in the exemplary embodiment, configurations from which those several configuration requirements have been omitted can also be extracted as inventions as long as effects are obtained.

Further, in the above exemplary embodiment, a case in which the electric charge storage period resulting from the radiation detector 60 is made fixed in a predetermined period per imaging site has been described, but embodiments are not limited to this. For example, an embodiment may also be given a configuration in which the electric charge storage period is appropriately set in accordance with, for example, the purpose of the radiographic image that has been obtained by imaging. In this case, convenience can be improved even more.

Further, in the above exemplary embodiment, an example in which, prior to performing the electric charge storage resulting from the radiation detector 60, the CPU 92A repeats the reset action until it receives the instruction data instructing it to start executing the imaging action has been described as an example, but embodiments are not limited to this. For example, the invention may also be configured such that, in a case in which the CPU 92A has received the instruction data, the CPU 92A performs the reset action once immediately before starting the electric charge storage resulting from the radiation detector 60 and then transitions to the electric charge storage state. Further, in a case in which the reset action is in the middle of being executed at the point in time when the CPU 92A has receive the instruction data, the CPU 92A may perform control so as to start the electric charge storage resulting from the radiation detector 60 at the point in time when the reset action has ended.

Further, in the above exemplary embodiment, a case in which communication is performed wirelessly between the electronic cassettes 32 and the console 42 and between the radiation generator 34 and the console 42 has been described, but embodiments are not limited to this and may also, for example, be given a configuration in which communication between at least one of these is performed via wires.

Further, in the above exemplary embodiment, a case in which the CPU 104 acquires the offset image data as the same electric charge storage period as when performing capture of a radiographic image has been described, but embodiments are not limited to this. For example, an embodiment may also be given a configuration in which the CPU 104 applies a period shorter than the electric charge storage period when performing capture of a radiographic image, acquires the offset image data, and multiples the acquired offset image data by a coefficient corresponding to the shortened electric charge storage period to thereby correct and apply the offset image data. In this case, the period for acquiring the offset image data can be shortened.

Further, in the above exemplary embodiment, a case in which the CPU 104 acquires the offset image data immediately before performing actual capture of a radiographic image after the imaging menu has been input has been described, but embodiments are not limited to this. For example, an embodiment may also be given a configuration in which the CPU 104 acquires the offset image data beforehand in each of mutually different plural electric charge storage periods and applies the offset image data that has been acquired in the electric charge storage period closet to or the same as the time of actual capture of a radiographic image. In this case, the offset image data can be acquired beforehand, so processing for acquiring the offset image data immediately after the imaging menu has been input can be omitted, and the processing burden at the time of capture of a radiographic image can be alleviated.

Further, in the above exemplary embodiment, an example in which the CPU 104 generates the composite image data by using the offset image data of each of the electronic cassettes 32 to correct each of the sets of subject image data that have been acquired for each of the electronic cassettes 32 and combining the subject image data has been described, but embodiments not limited to this. For example, an embodiment may also be configured such that the CPU 104 uses composite offset image data in which the offset image data of each of the electronic cassettes 32 have been combined to correct composite image data generated by combining the subject image data before correction.

In addition, the configuration of the RIS 10, the configuration of the electronic cassettes 32, and the configuration of the imaging systems 18 described in the above exemplary embodiment are examples, and unnecessary portions can be omitted therefrom, new portions can be added thereto, and states of connection and so forth can be changed in a scope not departing from the gist of the present invention.

Further, the flows of processing by the programs (see FIG. 5 and FIG. 7) described in the above exemplary embodiment are also examples, and unnecessary steps can be omitted therefrom, new portions can be added thereto, and the processing order can be switched around in a scope not departing from the gist of the present invention.

Moreover, the imaging menu input screen (see FIG. 6) described in the above exemplary embodiment is also an example, and the display content can be changed in a scope not departing from the gist of the present invention.

What is claimed is:

1. A radiographic image capture system comprising:
a radiographic image capture section in which a plurality of radiographic imaging devices are placed adjacent to each other in a predetermined direction, with each of the radiographic imaging devices independently performing an imaging action in which the radiographic imaging device detects radiation that has been applied from a radiation source and has passed through a subject to acquire image data representing a radiographic image of the subject, a preparatory action that is performed before the imaging action, and a transition action in which the radiographic imaging device transitions, in response to a transition command, from a first state in which the radiographic imaging device performs the preparatory action to a second state in which the radiographic imaging device performs the imaging action;

an output section that outputs the transition command to the plurality of radiographic imaging devices in a case in which imaging condition data has been input;

a generation section that combines image data acquired by each of the radiographic imaging devices transitioned to the second state by the transition command, to generate elongated image data representing an elongated radiographic image;

an acquisition section that acquires correction image data as a result of imaging being performed by the radiographic imaging devices in a state in which the radiation from the radiation source is not made incident thereon; and a correction section that corrects the image data or the elongated image data using the correction image data, wherein the correction image data is acquired each time before a plurality of sets of radiographic image data are acquired by the plurality of radiographic imaging devices, and the correction image data is used for offset correction.

2. The radiographic image capture system according to claim 1, wherein the preparatory action comprises repeatedly performing, until the transition command is input, a reset action in which electric charges stored in the radiographic imaging devices are discharged.

3. The radiographic image capture system according to claim 1, wherein the radiographic imaging devices are portable radiographic imaging devices.

4. The radiographic image capture system according to claim 1, wherein the correction image data is acquired during an electric charge storage period that is the same as an electric charge storage period for acquiring the plurality of sets of radiographic image data.

5. A radiographic image capture method comprising:

providing a plurality of radiographic imaging devices in a state in which the radiographic imaging devices are placed adjacent to each other in a predetermined direction, with each of the radiographic imaging devices independently performing an imaging action in which the radiographic imaging device detects radiation that has been applied from a radiation source and has passed through a subject to acquire image data representing a radiographic image of the subject, a preparatory action that is performed before the imaging action, and a transition action in which the radiographic imaging device transitions, in response to a transition command, from a first state in which the radiographic imaging device performs the preparatory action to a second state in which the radiographic imaging device performs the imaging action;

outputting the transition command to the plurality of radiographic imaging devices in a case in which imaging condition data has been input;

combining image data acquired by each of the radiographic imaging devices transitioned to the second state by the transition command to generate elongated image data representing an elongated radiographic image;

acquiring correction image data as a result of imaging being performed by the radiographic imaging devices in a state in which the radiation from the radiation source is not made incident thereon; and correcting the image data or the elongated image data using the correction image data, wherein the correction image data is acquired each time before a plurality of sets of radiographic image data are acquired by the plurality of radiographic imaging devices, and the correction image data is used for offset correction.

6. The radiographic image capture method according to claim 5, wherein the preparatory action comprises repeatedly performing, until the transition command is input, a reset action in which electric charges stored in the radiographic imaging devices are discharged.

7. The radiographic image capture method according to claim 5, wherein the radiographic imaging devices are portable radiographic imaging devices.

8. The radiographic image capture method according to claim 5, wherein the correction image data is acquired during an electric charge storage period that is the same as an electric charge storage period for acquiring the plurality of sets of radiographic image data.

* * * * *